(12) United States Patent
Li et al.

(10) Patent No.: US 9,921,222 B2
(45) Date of Patent: Mar. 20, 2018

(54) HISTOLOGICAL MARKERS FOR IDENTIFYING NON-SMALL CELL LUNG CARCINOMA PATIENTS FOR TREATMENT WITH AN ANTI-EGFR DRUG

(71) Applicant: CROWN BIOSCIENCE, INC. (Taicang), Taicang (CN)

(72) Inventors: Henry Qixiang Li, Carlsbad, CA (US); Mengmeng Yang, Beijing (CN)

(73) Assignee: CROWN BIOSCIENCE, INC. (TAICANG), Jiangsu Province (CN)

( * ) Notice: Subject to any disclaimer, the term of this patent is extended or adjusted under 35 U.S.C. 154(b) by 0 days.

(21) Appl. No.: 14/418,684

(22) PCT Filed: Jul. 31, 2013

(86) PCT No.: PCT/US2013/053091
§ 371 (c)(1),
(2) Date: Jan. 30, 2015

(87) PCT Pub. No.: WO2014/028221
PCT Pub. Date: Feb. 20, 2014

(65) Prior Publication Data
US 2015/0168411 A1 Jun. 18, 2015

(30) Foreign Application Priority Data
Jul. 31, 2012 (WO) ................ PCT/CN2012/079399

(51) Int. Cl.
*G01N 33/574* (2006.01)
*C07K 16/28* (2006.01)
*A61K 39/395* (2006.01)
*A61K 45/06* (2006.01)
*A61K 39/00* (2006.01)

(52) U.S. Cl.
CPC . *G01N 33/57423* (2013.01); *A61K 39/39558* (2013.01); *A61K 45/06* (2013.01); *C07K 16/2863* (2013.01); *A61K 2039/505* (2013.01); *A61K 2039/55* (2013.01); *C07K 2317/24* (2013.01); *G01N 2333/71* (2013.01); *G01N 2333/912* (2013.01); *G01N 2800/52* (2013.01)

(58) Field of Classification Search
CPC ......... G01N 33/57423; G01N 2800/52; A61K 16/2863
See application file for complete search history.

(56) References Cited

U.S. PATENT DOCUMENTS

2011/0081651 A1 4/2011 Hillan
2011/0118298 A1 5/2011 Fritz et al.

OTHER PUBLICATIONS

Ilson et al. "A phase 2 trial of erlotinib in patients with previously treated squamous cell and adenocarcinoma of the esophagus", *Cancer,* 117(2011):1409-1414.
Krumbach et al. "Primary resistance to cetuximab in a panel of patient-derived tumour xenograft models: activation of MET as one mechanism for drug resistance." European Journal of Cancer 47.8 (2011): 1231-1243, Abstract.
International Search Report based on International Patent Application No. PCT/US2013/053091, dated Dec. 16, 2013.
Written Opinion based on International Patent Application No. PCT/US2013/053091, dated Dec. 16, 2013.
Pirker et al. "Cetuximab plus chemotherapy in patients with advanced non-small-cell lung cancer (FLEX): an open-label randomized phase III trial", Lancet. May 2, 2009;373(9674):1525-31.
English translation of Examination Report in related Chinese Patent Application Serial No. 201380015223.9, dated Aug. 4, 2016.
Khambata-Ford et al. "Analysis of Potential Predictive Markers of Cetuximab Benefit in BMS099, a Phase III Study of Cetuximab and First-Line Taxane/Carboplatin in Advanced Non-Small-Cell Lung Cancer", *Journal of Clinical Oncology,* 28(6): 918-927, Feb. 20, 2010.
Pirker et al., "Prognostic factors in patients with advanced non-small cell lung cancer: Data from the phase III FLEX study", *Lung Cancer,* 77(2):376-382, Mar. 15, 2012.
Li, "Patient selection in non-small cell lung cancer: Histologic versus molecular subtypes?", *Journal of Thoracic Disease,* 2(4): 189-191, Dec. 1, 2010.
Leighl, "Treatment paradigms for patients with metastatic non-small-cell lung cancer: first-, second-, and third-line", *Current Oncology,* 19:52-58, Jun. 12, 2012.
Lynch et al. "Cetuximab and First-Line Taxane/Carboplatin Chemotherapy in Advanced Non-Small-Cell Lung Cancer: Results of the Randomized Multicenter Phase III Trial BMS099", *Journal of Clinical Oncology,* 28(6): 911-917, Feb. 20, 2010.
Yang, "Squamous non-small cell lung cancer (NSCLC-SCC) patient-derived xenografts (PDX) from Asian Patients have high response rate (RR) to cetuximab than those of adenocarcinoma", Oct. 29, 2013 http://www.crownbio.com/wp-content/uploads/EORTC_2013_poster_abstract_493-Squamous_non-small_cell_lung_cancerNSCLC-SCCpatient-derived_xenografts_PDX_from_Asian_patients.pdf.

(Continued)

*Primary Examiner* — Ruixiang Li
(74) *Attorney, Agent, or Firm* — Cooley LLP

(57) ABSTRACT

The present invention provides methods for the treatment of lung cancer patients, especially NSCLC with SCC or PLC using a drug against EGFR, such as an anti-EGFR antibody treatment, e.g., cetuximab. In addition, the present invention provides methods for identification or selection of lung cancer patients for the treatment with a drug against EGFR, such as an anti-EGFR antibody treatment, e.g., cetuximab based on histological determinations.

2 Claims, 5 Drawing Sheets

(56) References Cited

OTHER PUBLICATIONS

Scagliotti et al. "The Role of Histology with Common First-line Regimens for Advanced Non-small Cell Lung Cancer: A Brief Report of the Retrospective Analysis of a Three-arm Randomized Trial", *Journal of Thoracic Oncology,* 4(12): 1568-1571, Dec. 1, 2009.

European Search Report based on European Patent Application No. 13829184, dated Feb. 11, 2016.

English translation of Examination Report in related Japanese Patent Application Serial No. 2015-525570, dated Feb. 9, 2017.

HISTOLOGICAL MARKERS FOR IDENTIFYING NON-SMALL CELL LUNG CARCINOMA PATIENTS FOR TREATMENT WITH AN ANTI-EGFR DRUG

CROSS-REFERENCE TO RELATED APPLICATIONS

The present application is the national stage of International Patent Application PCT/US2013/053091, filed on Jul. 31, 2013, which claims priority to International Patent Application No. PCT/CN2012/079399, filed on Jul. 31, 2012, each of which is incorporated herein by reference in its entirety.

FIELD OF THE INVENTION

The present invention relates to treatment of lung cancer patients as well as identification and selection of lung cancer patients for treatment with a drug against epidermal growth factor receptor (EGFR), such as anti-EGFR antibody treatments, e.g., cetuximab.

BACKGROUND

Non-small cell lung cancer (NSCLC) is a common cancer with leading mortality globally but with few effective treatment options. NSCLC are also diverse types of diseases with major subtypes of adenocarcinoma (ADC, 40%), squamous cell carcinoma (SCC, 25~30%), undifferentiated large cell carcinoma (LCC, 10~15%), adenosquamous carcinoma (pleiomorphic carcinoma or PLC), sarcomatoid carcinoma (<5%), and others. Newly approved targeted therapies (NSCLC) have brought new hopes, including tyrosine kinase inhibitors (TKIs) targeting EGFR (e.g. erlotinib, gefitinib, etc.) and ALK (crizotinib). However, two major challenges limit the uses of these medicines. First, only small subsets of NSCLC patients respond to the treatments. Patients with EGFR activating mutations (~10%), more frequently found in Asian women, more likely respond to EGFR-TKIs (Lynch T J, et al. *N Engl J Med.* 2004; 350: 2129-39 and Paez J G, et al. *Science.* 2004; 304:1497-500), and patients with ALK-EML4 fusion (3~5%) more likely respond to crizotinib (Rodig S J, et al. *Curr Opin Investig Drugs.* 2010; 11:1477-90). Second, the treatments always result in rapid development of drug resistance (Gazdar A F, *Oncogene.* 2009; 28 Suppl 1:S24-31; Bean J, et al. *Proc Natl Acad Sci USA.* 2007; 104:20932-7; and Kubo T, et al. *Int J Cancer.* 2009; 124:1778-84). Therefore, new targeted medicine is urgently needed to compensate the existing target treatments. There remains a need in the art for effective therapies to NSCLC.

The methods of the present invention meet this need and provide methods for effective treatment of NSCLC.

SUMMARY OF THE INVENTION

The present invention provides methods for treating lung cancer. In some embodiments, the lung cancer is non-small cell lung carcinoma (NSCLC). In some embodiments, the NSCLC is a NSCLC with certain histology, e.g., NSCLC with squamous cell carcinoma (SCC) or adenosquamous carcinoma (pleiomorphic carcinoma or PLC). In one embodiment, the present invention provides methods for treating a patient with lung cancer by administering to the patient an effective amount of a drug. In some embodiments, the drug is against epidermal growth factor receptor (EGFR). In some embodiments, the drug is targeting EGFR. In some embodiments, the drug is targeting the signaling pathway downstream of EGFR. In some embodiments, the drug is an antagonist or an antibody of the ligand of EGFR, for example, an antagonist or an antibody of epidermal growth factor (EGF), transforming growth factor α (TGFα), HB-EGF, amphiregulin, betacellulin, epigen, and/or epiregulin. In some embodiments, the drug is a small molecule. In some embodiments, the drug is against a heterodimer formed by EGFR and another member of the ErbB receptor family such as EfbB2/Her2/neu. In some embodiments, the drug is against a homodimer formed by EGFRs. In some embodiments, the drug is an antibody or antibody like therapeutic entity against EGFR (anti-EGFR antibody treatment), e.g., cetuximab. In another embodiment, the present invention provides methods for treating a patient with lung cancer, such as NSCLC by determining the histology of the NSCLC and treating a patient with an antibody against EGFR, e.g., cetuximab when the NSCLC is squamous cell carcinoma (SCC) or adenosquamous carcinoma (PLC).

In another embodiment, the present invention provides methods for identifying responder and/or nonresponder lung cancer patients to a treatment against EGFR comprising determining the histology of the lung cancer in a biological sample from a patient with lung cancer, wherein a determination that the lung cancer is NSCLC, and the NSCLC is SCC or PLC is indicative of a responder to a treatment against EGFR, e.g., cetuximab treatment and a determination that the NSCLC is adenocarcinoma (ADC) or large cell carcinoma (LCC) is indicative of a nonresponder to the treatment against EGFR, e.g., cetuximab treatment.

In another embodiment, the present invention provides methods for determining a treatment regimen for treating lung cancer in a patient in need thereof. The method includes determining the histology of lung cancer in a biological sample from a patient with lung cancer, wherein a determination that said lung cancer is NSCLC, and the NSCLC is SCC or PLC is indicative of a responder to the treatment against EGFR, e.g., cetuximab treatment and a determination that the NSCLC is ADC or LCC is indicative of a nonresponder to the treatment against EGFR, e.g., cetuximab treatment, and treating said patient with a treatment against EGFR, e.g., cetuximab when the NSCLC is SCC or PLC.

In another embodiment, the present invention provides methods for altering or modifying the treatment regimen of a treatment against EGFR, e.g., cetuximab comprising determining the histology of the lung cancer in a biological sample from a patient with lung cancer receiving a treatment, e.g., the standard of care lung cancer treatment or cetuximab and altering the treatment regimen based on the histology of the lung cancer. For example, the treatment regimen of a treatment against EGFR, e.g., cetuximab is continued when said lung cancer is NSCLC, and the NSCLC is SCC or PLC or said treatment regimen is discontinued when said NSCLC is ADC or LCC.

The present invention provides methods for selecting a patient with lung cancer for treatment with a treatment against EGFR, e.g., cetuximab comprising determining the histology of the lung cancer in a biological sample from a patient, wherein a determination that the lung cancer is NSCLC, and the NSCLC is SCC or PLC is indicative of a responder to the treatment against EGFR, e.g., cetuximab treatment and a determination that the NSCLC is ADC or LCC is indicative of a nonresponder to the treatment against EGFR, e.g., cetuximab treatment, and selecting for treatment with the drug against EGFR, e.g., cetuximab those patients determined to have SCC or PLC.

The present invention provides methods for providing useful information for determining or evaluating the treatment of lung cancer with a drug against EGFR, e.g., cetuximab. The method includes determining the histology of the lung cancer in a biological sample from a patient and providing the determination of the histology to an entity that provides a determination or evaluation of the treatment based on the histology of the lung cancer. In some embodiments, the lung cancer is a NSCLC.

The present invention provides for kits. The kits include one or more reagents suitable for determining the histology of a lung cancer, and optionally an instruction for using the histology results for the determination of lung cancer treatment, e.g., when the lung cancer is a NSCLC, and the NSCLC is SCC or PLC the determination is indicative of a responder and when the NSCLC is ADC or LCC the determination is indicative of a nonresponder to a drug against EGFR, e.g., cetuximab.

BRIEF DESCRIPTION OF THE DRAWINGS

FIG. 2A depicts the IHC images, and FIG. 2B is a bar graph showing the IHC scores.

DETAILED DESCRIPTION OF THE INVENTION

Figure 1:
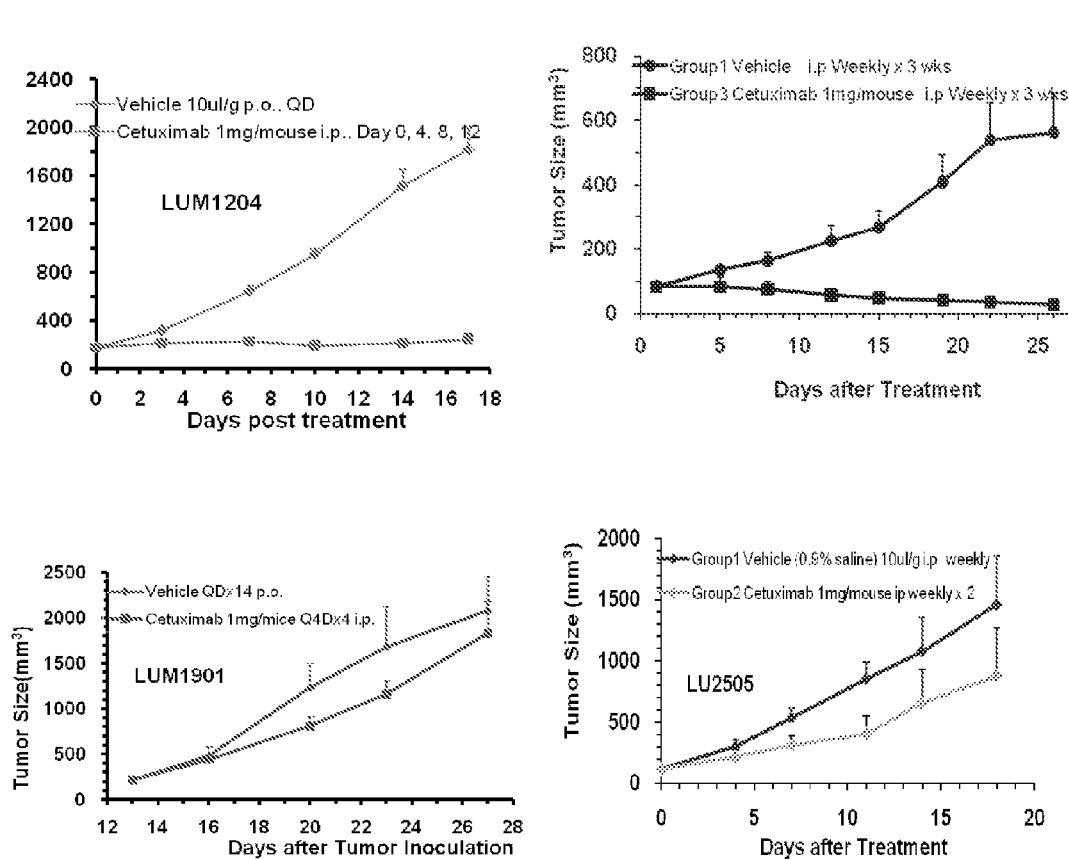
FIG. 1 shows the response to cetuximab by representative NSCLC-HuPrime models. Tumor size of the vehicle control (circles) and 1 mg/mouse cetuximab (squares) are shown for LU1204 (SCC), LU2505 (ADC), LU1901 (LCC), and LU1235 (PLC). LU1235 was described previously.

The present invention is based in part on the discovery that anti-EGFR antibody treatment is effective for the treatment of NSCLC, especially NSCLC with certain histology subtype. Accordingly the present invention provides methods for the treatment of NSCLC patients, especially NSCLC with SCC or PLC with a drug against EGFR.

According to the invention, "a drug against EGFR" refers to a composition which can modify the activity of EGFR signaling pathway, such as a composition that can increase, decrease, eliminate, enhance, delay, reduce, or block the activity of EGFR signaling pathway. In some embodiments, the composition is directly against EGFR, or one or more components in EGFR signaling pathway, at DNA level, transcriptional level, translational level, post-translational level, and/or protein level. The composition can specifically target EGFR, or target at least EGFR. In some embodiments, the composition can cause gene suppression and/or gene silencing of EGFR and/or a component in EGFR signaling pathway, e.g., knocking down or knocking out EGFR and/or a component in EGFR signaling pathway. In some embodiments, the composition can modify EGFR protein activity, such as modifying the EGFR binding activity to its ligand and/or its ability to induce downstream signaling pathways. In some embodiments, the drug is an antagonist or an antibody of the ligand of EGFR, for example, an antagonist or an antibody of epidermal growth factor (EGF), transforming growth factor α (TGFα), HB-EGF, amphiregulin, betacellulin, epigen, and/or epiregulin. In some embodiments, the drug can target to EGFR and/or the ligand and block ligand-receptor binding. In some embodiments, the drug can cause confirmation changes in the receptor and/or the ligand and reducing or inactivating EGFR mediated cell signaling. In some embodiments, the drug is against a heterodimer formed by EGFR and another member of the ErbB receptor family such as EfbB2/Her2/neu, or a homodimmer formed by two EGFR molecules. EGFR signaling pathway is described in Sechacharyulu et al. (Targeting the EGFR signaling pathway in cancer therapy, Expert Opin Ther Targets, 2012 January; 16(1): 15-31.), Oda et al. (A comprehensive pathway map of epidermal growth factor receptor signaling, Molecular Systems Biology 1:2005.0010), and Development EGFR Signaling Pathway (Pathway Maps, Thomson Reuters, 2012), each of which is incorporated herein in its entirety for all purposes.

In some embodiments, the drug comprises a small molecule. As used herein, the term "small molecule" refers to a molecule having a molecular weight of less than 500 MW, wherein the drug is a non-peptidyl or peptide agent. In some embodiments, the drug comprises a protein or a polypeptide. In some embodiments, the drug comprises a hybrid molecule. In some embodiments, the drug is an antibody. In some embodiments, the drug is an anti-EGFR antibody. In some embodiments, the drug is an anti-EGFR ligand antibody. In some embodiments, the drug is a humanized anti-EGFR ligand antibody. In some embodiments, the antibody is a monoclonal antibody.

In some embodiments, the drug is an anti-EGFR antibody. In some embodiments, the drug is Cetuximab or functional variants or derivatives thereof. None limiting examples of anti-EGFR antibodies have been described in PCT publication Nos. WO/2011/140151, WO/2007/058823, WO/2011/080209, WO/2010/080463, WO/2012/020059, WO/2011/080209, WO/2011/059762, WO/2011/152525, WO/2011/140254, WO/2010/034441, WO/2011/156617, WO/2005/090407, WO/2013/006547, WO/2008/140493, WO/2011/156617, U.S. Pat. Nos. 5,942,602, 6,129,915, 7,723,484, 7,618,631, 7,598,350, and U.S. Patent Application Publication Nos. 20100166755, 20080274114, 20130142812, 20110158987, 20120107234, 20110117110, 20110287002, 20120149879, 20120282633, 20100009390, 20050238640, 20060154334, 20120231021 and 20130149299, each of which is incorporated herein by reference in its entirety for all purposes.

In addition, the present invention also provides methods for selecting NSCLC patients for certain anti-EGFR antibody treatment based on patients' histology subtype, e.g., NSCLC with SCC or PLC is suitable for treatment against EGFR, such as the anti-EGFR antibody treatment, e.g., cetuximab. According to the present invention, the term "a treatment against EGFR" refers to a treatment using a drug against EGFR.

In one embodiment, the present invention provides methods for treating lung cancer in patients comprising determining the histology of the lung cancer. In one embodiment, the method further comprises treating the patients with a drug against EGFR when the lung cancer is NSCLC, and the NSCLC is squamous cell carcinoma (SCC) or adenosquamous carcinoma (pleiomorphic carcinoma or PLC). In one embodiment, the method comprises treating a patient with a drug against EGFR. In some embodiments, the drug against EGFR is an anti-EGFR antibody, such as cetuximab or functional variants thereof.

In another embodiment, the present invention provides methods for identifying responder and nonresponder patients comprising determining the histology of lung cancer in a biological sample from a patient with lung cancer, wherein a determination that said lung cancer is NSCLC, and the NSCLC is SCC or PLC is indicative of a responder to a treatment against EGFR, such as an anti-EGFR antibody treatment, e.g., cetuximab treatment and a determination that the NSCLC is adenocarcinoma (ADC) or large cell carcinoma (LCC) is indicative of a nonresponder to a treatment against EGFR, such as an anti-EGFR antibody treatment, e.g., cetuximab treatment.

In another embodiment, the present invention provides methods for determining a treatment regimen for treating lung cancer in a patient in need thereof. The method includes determining the histology of the lung cancer in a biological sample from a patient with NSCLC. A determination that the lung cancer is NSCLC, and the NSCLC is SCC or PLC indicates a responder to a treatment against EGFR, such as an anti-EGFR antibody treatment, e.g., cetuximab treatment and a determination that the NSCLC is ADC or LCC indicates a nonresponder to a treatment against EGFR, such as an anti-EGFR antibody treatment, e.g., cetuximab treatment. The patient is then treated with a treatment against EGFR, such as an anti-EGFR antibody treatment, e.g., cetuximab when the NSCLC is SCC or PLC.

In another embodiment, the present invention provides methods for altering or modifying the treatment regimen of a treatment against EGFR for a patient with lung cancer, such as an anti-EGFR antibody treatment, e.g., cetuximab comprising determining the histology of lung cancer in a biological sample from a patient with lung cancer receiving the standard of care for lung cancer or a treatment against EGFR, such as an anti-EGFR antibody treatment, e.g., cetuximab and altering or modifying the treatment regimen based on the histology of the lung cancer. For example, the treatment regimen is continued for a treatment against EGFR, such as an anti-EGFR antibody treatment, e.g., cetuximab when said lung cancer is NSCLC, and the NSCLC is SCC or PLC or the treatment regimen for a treatment against EGFR, such as an anti-EGFR antibody treatment, e.g., cetuximab is discontinued when said NSCLC is ADC or LCC.

In another embodiment, the present invention provides methods for selecting a patient with lung cancer for treatment with a drug against EGFR, such as an anti-EGFR antibody treatment, e.g., cetuximab comprising determining the histology of lung cancer in a biological sample from a patient. A determination that the lung cancer is NSCLC, and the NSCLC is SCC or PLC indicates a responder to a treatment against EGFR, such as an anti-EGFR antibody treatment, e.g., cetuximab treatment and a determination that the NSCLC is ADC or LCC indicates a nonresponder to a treatment against EGFR, such as an anti-EGFR antibody treatment, e.g., cetuximab treatment. Patients determined to have SCC or PLC are selected for a treatment against EGFR, such as a treatment with anti-EGFR antibody treatment, e.g., cetuximab.

A histological determination that the lung cancer is NSCLC, and the NSCLC is SCC or PLC indicates a responder to a treatment against EGFR, such as an anti-EGFR antibody treatment, e.g., cetuximab treatment. A histological determination that the NSCLC is ADC or LCC indicates a nonresponder to a treatment against EGFR, such as an anti-EGFR antibody treatment, e.g., cetuximab treatment. In some embodiments, the lung cancer histological determination is made prior to a treatment against EGFR, such as an anti-EGFR antibody treatment, e.g., cetuximab treatment. In some embodiments, the lung cancer histological determination is made during a treatment against EGFR, such as an anti-EGFR antibody treatment, e.g., cetuximab treatment. In some embodiments, the lung cancer histological determination is made after a treatment against EGFR, such as an anti-EGFR antibody treatment, e.g., cetuximab treatment.

A responder according to the present invention is an individual who exhibits treatment efficacy and a nonresponder does not exhibit treatment efficacy. The phrase "determining the treatment efficacy" or "determining the efficacy of treatment" and variants thereof can include any methods for determining that a treatment is providing a benefit to a subject. The term "treatment efficacy" and variants thereof are generally indicated by alleviation of one or more signs or symptoms associated with the disease and can be readily determined by one skilled in the art. "Treatment efficacy" may also refer to the prevention or amelioration of signs and symptoms of toxicities typically associated with standard or non-standard treatments of a disease, i.e. chemotherapy or radiation therapy for the treatment of cancer. Determination of treatment efficacy is usually indication and disease specific and can include any methods known or available in the art for determining that a treatment is providing a beneficial effect to a patient. For example, evidence of treatment efficacy can include but is not limited to remission of the disease or indication, for cancer this can include but is not limited to a decrease or reduction in tumor size, in tumor metastasis, etc. Further, treatment efficacy can also include general improvements in the overall health of the subject, such as but not limited to enhancement of patient life quality, increase in predicted subject survival rate, decrease in depression or decrease in rate of recurrence of the indication (increase in remission time). (See, e.g., *Physicians' Desk Reference* (2010).)

An anti-EGFR antibody treatment can include any treatment using anti-EGFR antibody or antibody like therapeutics including without any limitation any molecule with one or more anti-EGFR CDRs. In one embodiment, anti-EGFR antibody treatment includes any approved anti-EGFR antibody, e.g., cetuximab (also known as erbitux) or biosimilar or derivatives thereof, e.g., fully human anti-EGFR antibody, etc. Cetuximab (marketed in North America by ImClone and Bristol-Myers Squibb and in the rest of the world by Merck KGaA) is a recombinant, human/mouse chimeric monoclonal antibody that blocks activation of the epidermal growth factor (EGF) receptor (EGFR). Cetuximab can be given by intravenous infusion for treatment of metastatic colorectal cancer and head and neck cancers. In some embodiments, cetuximab is formulated in a sterile colorless liquid of pH 7.0 to 7.4. In some embodiments, cetuximab is formulated at a concentration of 2 mg/mL in either 100 mg (50 mL) or 200 mg (100 mL). In some embodiments, cetuximab is formulated in single-use vials. In some embodiments, the cetuximab formulation includes 8.48 mg/mL sodium chloride, 1.88 mg/mL sodium phosphate dibasic heptahydrate, 0.41 mg/mL sodium phosphate monobasic monohydrate, and sterile water for injection. Methods and formulations for administering cetuximab are well known by those skilled in the medical art and any well known methods of administering cetuximab, dosing regimens for cetuximab or formulations for cetuximab are contemplated for use with the methods of the present invention. Detailed compositions and methods of using Cetuximab are described in U.S. Pat. Nos. 8,075,916, 7,977,336, 6,217,866, each of which is incorporated by reference in its entirety for all purposes.

Methods for determining histology of cancer are well known in the art and those skilled in the art can use any methods known for determining SCC, PLC, ADC or LCC histology of a cancer sample.

Squamous cell lung carcinoma (SCC) is typically a centrally located large cell cancer (non-small cell lung cancer or NSCLC) that often has a paraneoplastic syndrome causing ectopic production of parathyroid hormone-related protein (PTHrP), resulting in hypercalcemia. It is primarily due to smoking. SCC cells are large, flattened and stratified with a high cytoplasm to nucleus ratio. Key diagnostic features include the presence of intracytoplasmic keratin which may be linked to the presence of intercellular bridges and squamous pearl formation. Most SCC cells arise centrally within the main, lobar, segmental or subsegmental bronchi but some occur more peripherally. The tumour mass generally extends into the lumen of the airway with invasion into the underlying wall. Squamous cell carcinoma requires the presence of at least one of the following: keratin, keratin pearls or intercellular bridges.

Adenocarcinoma (ADC) of the lung is a common histological form of lung cancer that contains certain distinct malignant tissue architectural, cytological, or molecular features, including gland and/or duct formation and/or production of significant amounts of mucus. Adenocarcinoma is the most common type of lung cancer in lifelong non-smokers. Adenocarcinomas are highly heterogeneous tumors, and several major histological subtypes are currently recognized: acinar adenocarcinoma, papillary adenocarcinoma, bronchioloalveolar adenocarcinoma, solid adenocarcinoma with mucin production, and mixed types. Adenocarcinoma of the lung tends to stain mucin positive as it is derived from the mucus producing glands of the lungs. Similar to other adenocarcinoma, if this tumor is well differentiated (low grade) it will resemble the normal glandular structure. Poorly differentiated adenocarcinoma will not resemble the normal glands (high grade) and will be detected by seeing that they stain positive for mucin (which the glands produce). Adenocarcinoma requires the presence of a lepidic pattern (previously bronchioloalveolar pattern), acinar pattern (definite gland formation), papillary pattern, papillary nodules without stromal cores (micropapillary pattern) or intracellular mucin-containing vacuoles in more than five cells in two consecutive high power fields of an otherwise undifferentiated carcinoma (solid pattern). As most ADC are histologically heterogeneous, they generally fall into the mixed category. The tumours usually arise in the smaller peripheral airways (as distinct from the cartilage bearing bronchi) but they can be found more centrally. The key diagnostic features of ADC include gland formation—where the tumour cells are arranged around a central lumen—and/or mucin production.

Large-cell lung carcinoma (LCC) is a heterogeneous group of undifferentiated malignant neoplasms originating from transformed epithelial cells in the lung. LCC is, in effect, a "diagnosis of exclusion", in that the tumor cells lack light microscopic characteristics that would classify the neoplasm as a small-cell carcinoma, squamous-cell carcinoma, adenocarcinoma, or other more specific histologic type of lung cancer, for example, the cells of the lesion are not-columnar in shape, do not contain mucous, do not show squamous differentiation, and do not have neuroendocrine properties or small cell characteristics. LCC is differentiated from small-cell lung carcinoma (SCC) primarily by the larger size of the anaplastic cells, a higher cytoplasmic-to-nuclear size ratio, and a lack of "salt-and-pepper" chromatin. Tumours tend to consist of large cells with abundant cytoplasm, large nuclei and prominent nucleoli and they may occur peripherally or centrally. Variants of LCC include clear cell carcinoma, giant cell carcinoma and large cell neuroendocrine carcinoma (LCNEC). The newest revisions of the World Health Organization Histological Typing of Lung Cancer schema include several variants of LCC, including (a) basaloid, (b) clear cell, (c) lymphoepithelioma-like, (d) rhabdoid phenotype, and (e) large-cell neuroendocrine carcinoma. In addition, a "subvariant", called "combined large-cell neuroendocrine carcinoma", or c-LCNEC, is recognized under the new system. To be designated a c-LCNEC, the tumor must contain at least 10% LCNEC cells, in combination with at least 10% of other forms of NSCLC.

Pulmonary pleomorphic carcinoma is a rare epithelial tumor and has an aggressive clinical course. As few studies of pulmonary pleomorphic carcinoma have been described, see Kaira et al. (Pulmonary Pleomorphic Carcinoma: A Clinicopathological Study Including EGFR Mutation Analysis, Journal of Thoracic Oncology: April 2010—Volume 5—Issue 4—pp 460-465).

Any suitable test can be used to determine the histology of the cancer. Such test and examination include, but are not limited to, common signs and symptoms of lung cancer, homer syndrome, superior vena cava syndrome, paraneoplastic syndromes, medical history and physical exam, imaging tests, chest X-ray, computed tomography (CT) scan, magnetic resonance imaging (MRI) scan, positron emission tomography (PET) scan, bone scan, sputum cytology, needle biopsy, bronchoscopy, endobronchial ultrasound, endoscopic esophageal ultrasound, mediastinoscopy and mediastinotomy, thoracentesis, thoracoscopy, immunohistochemistry, molecular tests, blood tests, pulmonary function tests, or any suitable methods derived from thereof. None-limiting examples of methods for determining histology of cancer are described in Walter et al. (The Histology of Lung Cancer, Thorax, 1955, 10:107), Nicholson et al. (Standards and Datasets for Reportin Cancers Dataset for lung cancer histophathology reports ($3^{rd}$ Edition), The Royal College of Pathoglogists, April 2011), Travis et al., (International Association for the Study of Lung Cancer/American Thoracic Society/European Respiratory Society international multidisciplinary classification of lung adenocarcinoma. J Thorac Oncol 2011; 6:244-285.), World Health Organization. Tumours of the lung, pleura, thymus and heart. Lyons: IARC Press, 2004, Tan et al. (A 5-MicroRNA Signature for Lung Squamous Cell Carcinoma Diagnosis and hsa-miR-31 for Prognosis, Imaging, Diagnosis, Prognosis, DOI: 10.1158/1078-0432.CCR-11-0419), and Bishop et al. (p40 (ΔNp63) is Superior to p63 for the Diagnosis of Pulmonary Squamous Cell Carcinoma, Mod Pathol. 2012; 25(3):405-415), Iwasaki et al., (Pulmonary Pleomorphic Carcinoma: Diagnosis Using Small Biopsy Specimens, (Journal of Thoracic Oncology: September 2010—Volume 5—Issue 9—p 1492), each of which is herein incorporated by reference in its entirety for all purposes.

Methods for obtaining biological samples are well known in the art and any standard methods for obtaining biological samples can be employed. Biological samples that find use with the methods of the present invention include but are not limited to serum, blood, plasma, whole blood and derivatives thereof, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy. (See, e.g., Clinical Proteomics: Methods and Protocols, Vol. 428 in Methods in Molecular Biology, Ed. Antonia Vlahou (2008).) In one embodiment, the biological sample of the present invention includes any cell or tissue samples of lung, e.g., on site or circulating or migrating cells of NSCLC. In another embodiment, the biological sample of the present invention includes any extract or partial or whole fractionation of cell or tissue samples of lung, e.g., on site or circulating or migrating cells of NSCLC.

In some embodiments the patient suitable for the treatment by the methods of the present invention is of Asian descent. In some embodiments the patient is of Asian descent, has NSCLC exhibiting SCC or PLC histology. In some embodiments, the patient is of East Asian descent.

In some embodiments, anti-EGFR antibody treatment, e.g., cetuximab can be co-administered with one or more chemotherapeutics, radiation therapeutics, chemoradiation therapeutics, or targeted therapeutics.

In some embodiments, the chemotherapeutic includes but is not limited to vinblastine, vincristine, dactinomycin, daunorubicin, doxorubicin, etoposide, mithramycin, paclitaxel, docetaxel, cisplatin, carboplatin, fluorouracil, folinic acid and irinotecan.

In some embodiments, the targeted therapeutic includes but is not limited to bevacizumab, trastuzumab, erlotinib, panitumumab, sorafenib, infliximab, adalimumab, basiliximab, daclizumab and omalizumab.

In some embodiments, the radiation therapeutic is administered at a dosage of about 40 Gy to about 80 Gy. In some embodiments the dosage is about 50 Gy to about 70 Gy, in some embodiments, the dosage is about 50 Gy to about 65 Gy. In some embodiments, the radiation therapy is administered at a dosage of about 50 Gy, about 55 Gy, about 60 Gy or about 65 Gy.

In yet another embodiment, the present invention provides methods for providing useful information for predicting, determining, evaluating or monitoring the treatment or efficacy of treatment of NSCLC, e.g., with anti-EGFR antibody treatment, e.g., with cetuximab. The method includes determining the histology of NSCLC in a biological sample from a patient and providing the determination of the histology to an entity that provides determination, prediction, or evaluation of the treatment and/or the efficacy of the treatment based on the histology of the NSCLC. If the histology is SCC or PLC, the entity can provide a determination that treatment with anti-EGFR antibody treatment, e.g., cetuximab should be used or should be continued. If the histology is ADC or LLC, the entity can provide a determination that treatment with anti-EGFR antibody treatment, e.g., cetuximab should not be used or should be discontinued.

The present invention provides for kits. The kits include one or more reagents for determining the histology of the NSCLC and optionally with instructions for using the histology results for determining the treatment of NSCLC patients, e.g., with anti-EGFR antibody treatment. For example, when the NSCLC is SCC or PLC the determination indicates a responder and when the NSCLC is ADC or LCC the determination indicates a nonresponder of anti-EGFR antibody treatment.

EXAMPLES

Example 1: High Response Rate (RR) to Cetuximab by NSCLC-SCC PDX

Cetuximab has yet to be approved for treating non-small cell lung cancer (NSCLC), although several clinical trials indicated clinical benefit in some patients, because lack of a convincing predictive biomarker(s) for likely responders (Pirker R, et al. *Lancet*. 2009; 373:1525-31; Khambata-Ford S, et al. *J Clin Oncol*. 2010; 28:918-27; and O'Byrne K J, et al. *Lancet Oncol*. 2011; 12:795-805). To explore predictive biomarker of cetuximab response, we established a large collection of patient derived xenografts (PDX) from Asian patients with different NSCLC histology subtypes, including adenocarcinoma (ADC), squamous cell carcinoma (SCC), pleiomorphic carcinoma (PLC) and large cell carcinoma (LCC), etc. Interestingly, while NSCLC had overall take-rate of engraftment of 25%, SCC take rate was ~31%, near-double of the ~17% of ADC, a phenomenon may have biological implication for tumor metastatic potential and prognosis. When we tested cetuximab in a randomly selected cohort of 32 PDX models, we confirmed that a subset of them responded to cetuximab (15/32) (as defined by % $^{\Delta T}/_{\Delta C}$<50%, 47%). By carefully examining the histopathology along with molecular genetic traits of this cohort, we surprisingly found that all the responsive models exclusively belong to SCC and PLC (14/15 and 1/15 respectively), in contrast to none to ADC (0/15). In contrast, non-responders (% $^{\Delta T}/_{\Delta C}$>50%) are inclusive of ADC (7/17), LCC (2/17), and SCC (7/17). While none for responders, 1/7 non-responsive SCC has activating KRAS G12D mutation. One partial responder has ALK-EML4 fusion (% $^{\Delta T}/_{\Delta C}$=37%). In general, non-responsive or partially responsive SCC tend to have relatively lower EGFR expression as compared to good responders (%$^{\Delta T}/_{\Delta C}$<20%). Among the good responders are ones including activating EGFR mutations (deletion, insertion and point mutations). In summary, our data seem to suggest that Asian SCC has higher engraftment take-rate and higher cetuximab response rate (RR) than Asian ADC, with possibly positive factors of higher EGFR expression and mutation, and negative factors of KRAS mutation, ALK fusion and c-Met amplification.

While NSCL in general are considered aggressive diseases, between the two major histology subtypes, SCC is even more aggressive in terms of metastasis and poorer prognosis (What is non-small cell lung cancer, American Cancer Society, 2012). The tyrosine kinase inhibitors (TKIs) were believed to be more effective in treating adenocarcinoma than SCC, since the positive factor of EGFR mutations for benefit of TKI treatments are often associated with adenocarcinoma (20%~40%) (Pao et al, 2009 and Billah, et al 2011) and rarely with SCC (<3%) (Sequest L V et al., 2011). Because of the EGFR mutation tests were considered as predictive tests for TKI treatment of ADC, but not SCC (NCCN Clinical Practice Guideline), or in other words, TKIs have mostly been considered to be a treatment of ADC, exclusive of SCC. Consequently, there is essentially no apparent targeted treatment today for SCC. However, most clinical studies that led to this belief have largely been conducted in the West and on patients of Caucasian populations. How much these are true to Asian patients, e.g., Chinese NSCLC patients, remains to be determined.

All these render the extreme urgency of additional treatment options for NSCLC patients, particularly those marketed drugs but yet to be approved for this indication.

Among them are monoclonal antibodies against EGFR, the same target of the two approved NSCLC drugs (EGFR-TKIs), including cetuximab and panitumumab (also not approved Matuzumab) being such potential options.

Cetuximab is an IgG1 monoclonal antibody. It targets to EGFR and blocks ligand-receptor binding, causing confirmation changes in the receptor and inactivating EGFR mediated cell signaling (Mendelsohn J, et al. *J Clin Oncol.* 2003; 21:2787-99). It was approved by the US Food and Drug Administration (FDA) for treating EGFR-expressing metastatic colorectal carcinoma (mCRC), either as a single agent (for irinotecan-/oxaliplatin-refractory patients) or in combination with irinotecan (for irinotecan-refractory patients) (Ciardiello F, et al. *N Engl J Med.* 2008; 358:1160-74), excluding those with KRAS mutations at codons 12 and 13 (De Roock W, et al. *Lancet Oncol.* 2011; 12:594-603). Cetuximab is also approved for the indication of squamous cell carcinoma (SCC) of head and neck with locally advanced and in recurrent/metastatic disease as a combination treatment with chemotherapy (Vermorken J B, et al. *N Engl J Med.* 2008; 359:1116-27) and radiation (Bonner J A, et al. *N Engl J Med.* 2006; 354:567-78). However, it has not been approved for the treatment of NSCLC, although clinical trials (e.g., FLEX) have indicated antitumor activity in some patients when combined with chemotherapy agents (Pirker R, et al. *Lancet.* 2009; 373:1525-31). This is because of failure to identify a convincing predictive biomarker(s) for the likely responders (BMS099) (Khambata-Ford S, et al. *J Clin Oncol.* 2010; 28:918-27 and O'Byrne K J, et al. *Lancet Oncol.* 2011; 12:795-805), although recent efforts have suggested that higher EGFR-IHC scores demonstrated longer survival (Pirker R, et al. *Lancet Oncol.* 2012; 13:33-42).

Patient derived xenografts (PDX), without any in vitro manipulation, mirror patients' histopathological and genetic profiles including NSCLC PDX models (Ding L, et al. *Nature.* 2010; 464:999-1005; Marangoni E, et al. *Clin Cancer Res.* 2007; 13:3989-98; Nemati F, et al. *Clin Cancer Res.* 2010; 16:2352-62; Nemati F, et al. *Anticancer Drugs.* 2010; 21:25-32; Fichtner I, et al. *Clin Cancer Res.* 2008; 14:6456-68; and Hennessey P T, et al. *PLoS One.* 2011; 6:e20584). PDX has improved the predictive power of preclinical cancer models and enables discovery of predictive biomarkers for targeted therapeutics. Establishment of a large collection of PDX models (named as NSCLC HuPrime®) by engrafting naive Asian NSCLC patient tumor tissues into immunocompromised mice was previously described (Yang M, et al. Overcoming erlotinib resistance with tailored treatment regimen in patient-derived xenografts from naive Asian NSCLC patients In *J. Cancer.* 2013 Jan. 15:132(2): E74-84; Epub 2012 Oct. 3). This collection enabled the close examination of the nature of subtypes of NSCLC and also the ability to perform clinical trial-like studies based on a randomly selected cohort. We found that SCC subtype has significant high engraftment rate than ADC, also has high percentage of EGFR mutations rate, and in particular, has high response rate (RR) to cetuximab treatment—in the tested NSCLC models, all the responders so far are almost exclusively SCC, at least for the Asian patient derived models. Cetuximab treatment of a randomly selected cohort of the engrafted models demonstrated that not only a subset of them responded to the treatment, but also all the responders so far are surprisingly almost exclusively SCC, suggesting significantly higher response rate (RR) for SCC than non-SCC, at least for the Asian patients. In addition, we also identified a number of factors that might influence the response either positively or negatively. This discovery indicated that NSCLC-SCC cetuximab could be a good disease target for cetuximab, as well as other EGFR antagonistic monoclonal antibody drugs. These observations could potentially help to define the likely NSCLC cetuximab responders in the clinic for Asian patients.

Materials and Methods

Patient Tumor Samples, Engraftment in Immunocompromised Mice and Compound Efficacy Evaluation.

Engraftment of freshly and surgically removed tumor tissues from the patients diagnosed as NSCLC has been previously described (Yang M, et al. Overcoming drug resistance with tailored treatment regimen in patient derived xenografts from naïve Asian NSCLC patients resistant to EGFR inhibitors. 2012; submitted), and was approved by the Institutional Review Boards of Hebei Medical University Fourth Hospital, with the informed consents from patients. All studies involving experimental animals were carried out in strict accordance with the recommendations of the Guide for the Care and Use of Laboratory Animals of the National Institutes of Health. The protocol was approved by the Committee on the Ethics of Animal Experiments of Crown Bioscience, Inc. (Crown Bioscience IACUC Committee). The evaluation of antitumor activity of cetuximab in established NSCLC-PDX models was also previously described (Yang M, et al. Overcoming drug resistance with tailored treatment regimen in patient derived xenografts from naïve Asian NSCLC patients resistant to EGFR inhibitors. 2012; submitted). The tumor growth was monitored twice weekly, and % $^{\Delta T}/_{\Delta c}$ value were calculated for assessing tumor response to the treatment (ΔT=tumor volume change in the treatment group and ΔC=tumor volume change in control group).

Hotspot Oncogene Mutation Analysis.

EGFR gene hotspot analyses of NSCL-PDX models were previously described (Yang M, et al. Overcoming drug resistance with tailored treatment regimen in patient derived xenografts from naïve Asian NSCLC patients resistant to EGFR inhibitors. 2012; submitted). For other oncogene mutation analysis, the PCR primers were: KRAS-Exon 2, F: 5'-TTATGTGTGACAT GTTCTAAT-3' (SEQ ID NO: 1); R: 5'-AGAATGGTCCTGCACCAGTAA-3' (SEQ ID NO: 2). KRAS-Exon 3, F: 5'-TCAAGTCCTTTGCCCATTTT-3' (SEQ ID NO: 3); R: 5'TGCATGGCATTAGCAAAGAC-3' (SEQ ID NO: 4). KRAS-Exon 4, F: 5'-TTGTGGACAG-GTTTTGAAAGA-3' (SEQ ID NO: 5); R: 5'-AGAAGCAA TGCCCTCTCAAG-3' (SEQ ID NO: 6). EGFR-Exon 18, F: 5'-CATGGTGAGGGCTGAGGTGA-3' (SEQ ID NO: 7), R: 5'-CCCCACCAGACCATGAGAGG-3' (SEQ ID NO: 8). EGFR-Exon 19, F: 5'-GTGCATCGCTGGTAACATCCA-3' (SEQ ID NO: 9), R: 5'-GGAGATGAGCAGGGTCTA-GAGCA-3' (SEQ ID NO: 10). EGFR-Exon 20, F: 5'-CG-CATTCATGCGTCTTCACC-3' (SEQ ID NO: 11), R: 5'-CTATCCCAGGAGCGCAGACC-3' (SEQ ID NO: 12). EGFR-Exon 21, F: 5'-TGGCATGAACATGACCCTGAA-3' (SEQ ID NO: 13), R: 5'CAGCCTGGTCCCTGGTGTC-3' (SEQ ID NO: 14). PI3K-Exon 1. F: 5'-CTCCACGACCAT-CATCAGG-3' (SEQ ID NO: 15) R: 5'-GATTACGAAGG-TATTGGTTTAGACAG-3' (SEQ ID NO: 16). PI3K-Exon 9, F: 5'-GATTGGTTCTTTCCTGTCTCTG-3' (SEQ ID NO: 17), R: 5'-CCACAAATATCAATTTACAACCATTG-3' (SEQ ID NO: 18), PI3K-Exon 20: F: 5'-TGGGG-TAAAGGGAATCAAAAG-3' (SEQ ID NO: 19), R: 5'-CCTATGCAATCGGTCTTTGC-3' (SEQ ID NO: 20). AKT-Exon 3, F: 5'-ACATCTGTCCTGGCACAC-3' (SEQ ID NO: 21), R: 5'-GCCAGTGCTTGTTGCTTG-3' (SEQ ID NO: 22). BRAF-Exon 15, F: 5'-CTCTTCATAATGCTT-GCTC-3' (SEQ ID NO: 23), R: 5'-GTGAATACTGGGAAC- TATG-3' (SEQ ID NO: 24). ERK-Exon 2, F: 5'-ACTTTAC-CAACT TGCCTTCT-3' (SEQ ID NO: 25), R: 5'-TCACAACAAACCATCCCT-3' (SEQ ID NO: 26). ERK-Exon 8, F: 5'-TGCCTTACCCATAAC-3' (SEQ ID NO: 27), Reverse: 5'-GGACCTTGAGGAACATAAT-3' (SEQ ID NO: 28). PCR methods for these oncogenes are the same for EGFR mutation analysis as previously described (Yang M, et al. Overcoming drug resistance with tailored treatment regimen in patient derived xenografts from naïve Asian NSCLC patients resistant to EGFR inhibitors. 2012; submitted).

Expression and Gene Copy Analysis of EGFR and c-Met of NSCLC-HuPrime® Models.

The methods to determine the expression and gene copy numbers of EGFR and c-Met include standard immuno-histochemistry (IHC), Affy-U219, qRT-PCR, qPCR, SNP6 analysis, which were all previously described (Yang M, et al. Overcoming drug resistance with tailored treatment regimen in patient derived xenografts from naïve Asian NSCLC patients resistant to EGFR inhibitors. 2012; submitted).

Results

SCC Had Significantly Higher Engraftment Rate than ADC.

A large of panel of NSCLC PDX models was been established by transplanting surgically removed tumor tissues from treatment naïve Asian patients via subcutaneous engraftment in Balb/c nude mice (Yang M, et al. Overcoming drug resistance with tailored treatment regimen in patient derived xenografts from naïve Asian NSCLC patients resistant to EGFR inhibitors. 2012; submitted). The tumor tissues from hospitals and used for engraftment are of all NSCLC histopathology types without pre-inclusion or exclusion criteria, which consist of ~47% of adenocarcinoma (ADC), ~33% of squamous cell carcinoma (SCC), 3% of adenosquamous carcinoma (pleiomorphic carcinoma or PLC), 2% of large cell carcinoma (LCC), and 15% of others. The distribution ratio between ADC and SCC are roughly similar to in the patient population (see above). In general, the overall take-rate of 25% for NSCLC is consistent with those reported by others (Fichtner I. et al. *Clin Cancer Res.* 2008; 14:6456-68). Interestingly, the take-rate for SCC of ~31% is significantly higher than that of ADC (~17%). The take-rate for PLC (adenosquamous carcinoma) is ~35%, and LCC ~50% in this experiment, but the sample sizes for these two are too small to be meaningful. The statistically significant high take-rate of SCC (p-value of 0.002) over ADC has never been reported (Fichtner I, et al. *Clin Cancer Res.* 2008; 14:6456-68) and could imply underlying differences in tumor biology between these two major histology types, including more aggressive growth phenotypes and metastatic potentials for SCC than ADC in models and perhaps in patients (see above). It was reported that PDX more resembles to metastatic tumors than primary tumors (Ding L, et al. *Nature.* 2010; 464:999-1005), which could also explain the high take rate of SCC than ADC.

In order to ensure the histology of the models, the model tumor tissues were carefully reexamined by other pathologist independently and blindly. IHC staining was also performed for the differentiation markers to further confirm the histology of the models, which are summarized in Table 1 with representative images shown in FIG. 5.

TABLE 1

Patient Information.

| ID | Gender | Age | Stage | Grade | Histopathology |
|---|---|---|---|---|---|
| 9 | M | 47 | T2N1M0 IIb | II | Moderately to poorly differentiated SCC |
| 299 | M | 52 | T1N0M0 Ia | NA | Poorly differentiated SCC |
| 350 | M | 75 | T1N0M0 Ia | NA | Well differentiated squamous cell carcinoma |
| 377 | F | 45 | T1N0M0 I | III | Poorly differentiated ADC |
| 387 | F | 64 | T3N2M0IIIa | NA | Poorly differentiated adenocarcinoma |
| 395 | M | 58 | T1N2M0IIIa | NA | Poorly differentiated SCC |
| 697 | M | 53 | NA | NA | Poorly differentiated squamous cell carcinoma |
| 743 | M | 48 | NA | NA | Poorly differentiated squamous cell carcinoma |
| 858 | M | 55 | NA | NA | Poorly differentiated squamous cell carcinoma |
| 1143 | M | 85 | NA | NA | Poorly differentiated squamous cell carcinoma |
| 1155 | M | 77 | NA | NA | Moderately to poorly differentiated squamous cell carcinoma |
| 1160 | M | 70 | NA | NA | Poorly differentiated squamous cell carcinoma |
| 1215 | M | 58 | NA | NA | Squamous cell carcinoma, basaloid variant |
| 1225 | M | 53 | NA | NA | Poorly differentiated adenocarcinoma |
| 1245 | F | 57 | NA | NA | Moderately differentiated ADC |
| 1302 | M | 62 | NA | NA | Poorly differentiated squamous cell carcinoma |
| 1429 | M | 63 | NA | NA | Moderately-poorly differentiated SCC |
| 1513 | M | 65 | NA | NA | Poorly differentiated SCC |
| 1656 | F | 38 | NA | NA | Moderately differentiated SCC |
| 1901 | F | 65 | NA | NA | QC_diagnosis (P1, P2): Large cell undifferentiated carcinoma |
| 2503 | F | 78 | NA | NA | QC_diagnosis (P4): Poorly differentiated ADC |
| 2505 | M | 69 | NA | NA | Poorly differentiated adenocarcinoma |
| 2511 | M | 49 | NA | NA | Large cell undifferentiated carcinoma |
| 2512 | M | 58 | NA | NA | Poorly to moderately differentiated ADC |
| 330 | F | 72 | NA | II | Moderately to poorly differentiated squamous cell carcinoma |
| 357 | F | 60 | T1N0M0 Ia | NA | Moderately differentiated squamous cell carcinoma |
| 1235 | F | 56 | NA | NA | Adenosquamous carcinoma with part of bronchioloalveolar carcinoma |
| 1868 | M | NA | NA | NA | Poorly-moderately differentiated SCC |
| 1204 | M | 69 | NA | NA | QC_diagnosis (P2): Poorly differentiated squamous cell carcinoma |

TABLE 1-continued

Patient Information.

| ID | Gender | Age | Stage | Grade | Histopathology |
|---|---|---|---|---|---|
| 38 | M | 45 | T2N1M0 IIb | I-II | Poorly differentiated squamous cell carcinoma |
| 1219 | M | 70 | NA | NA | Poorly differentiated squamous cell carcinoma |
| 741 | M | 53 | NA | NA | Poorly differentiated squamous cell carcinoma |

A Subset of the Tested NSCLC-HuPrime® Cohort Responded to Cetuximab and were Found to be Exclusively SCC or PLC.

Thirty two NSCLC PDX models were used in the present cetuximab treatment study without intention of pre-selection per histopathology subtypes. They were four subtypes: SCC (22/32 or 66%), ADC (7/32 or 22%), PLC (1/32 or 3%) and LCC (3/32 or 9%) per histopathology examinations of the patient and the corresponding model samples (Table 2). The significant higher percentage of SCC was likely due to more SCC in the collection (see above).

Figure 2:
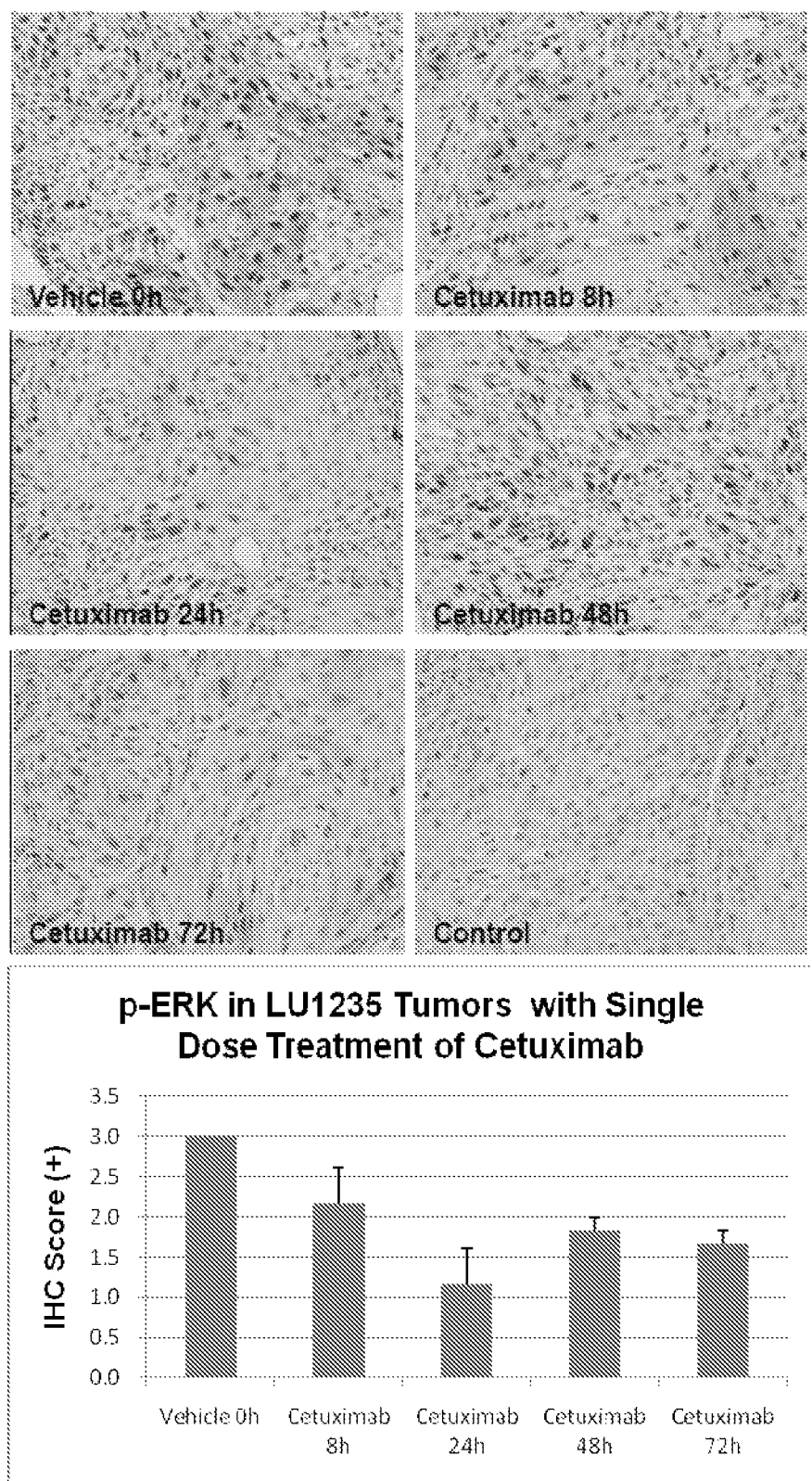
FIG. 2 shows the pharmacodynamic study of cetuximab in a representative NSCLC HuPrime® model. Single dose treatment with the cetuximab as described in FIG. 1, and the tumor samples were harvested at the time points as indicated for IHC analysis of the biomarker pERK.
Figure 3:
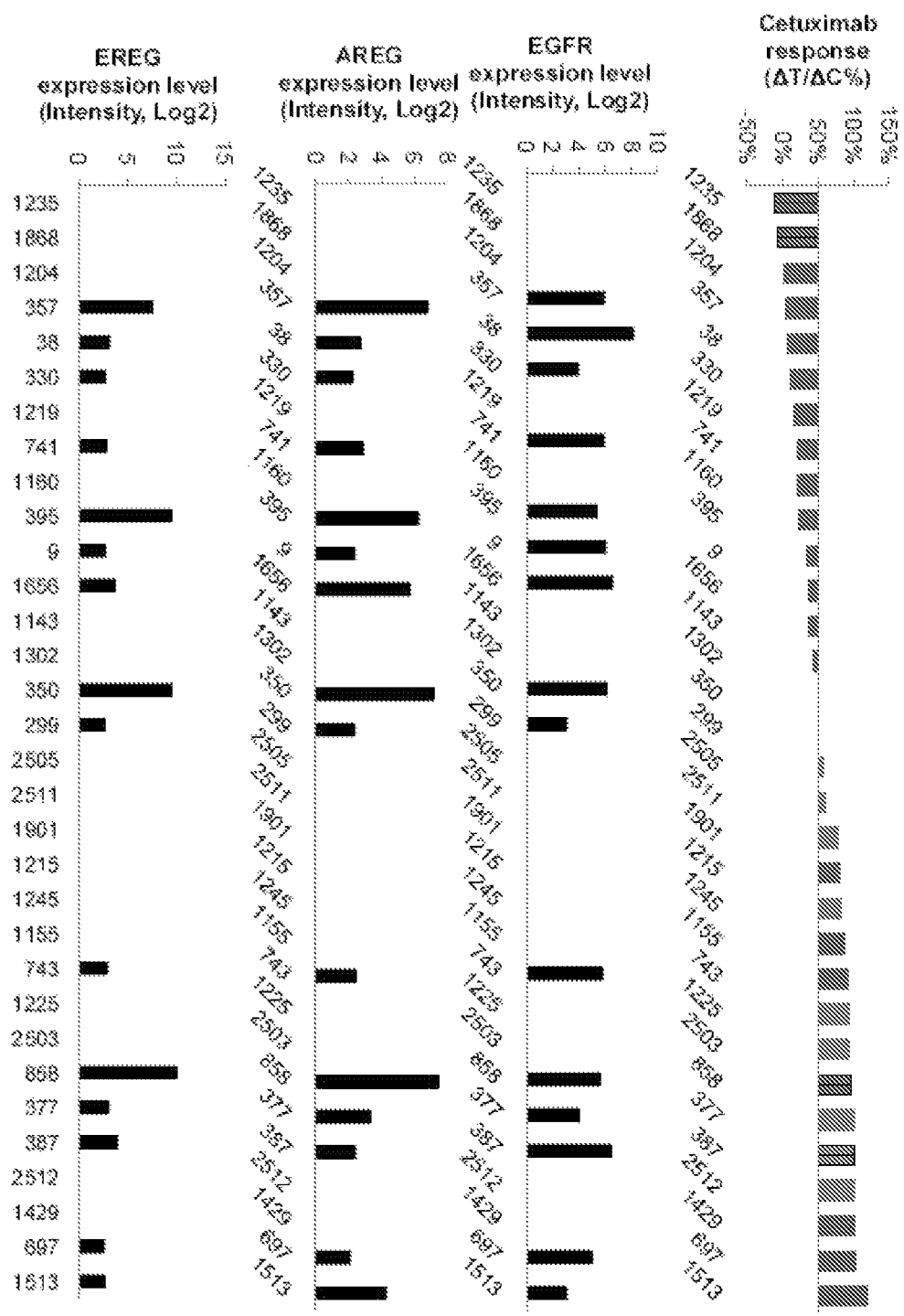
FIG. 3 shows the antitumor activity of cetuximab along with gene expression of EGFR, AREG and EREG. Panel from top to bottom: ΔT/ΔC. EGFR, AREG and EREG. Red blocks are for SCC and blue blocks are for non-SCC tumors. Blocks containing black boarder have EGFR mutation.
Figure 4:
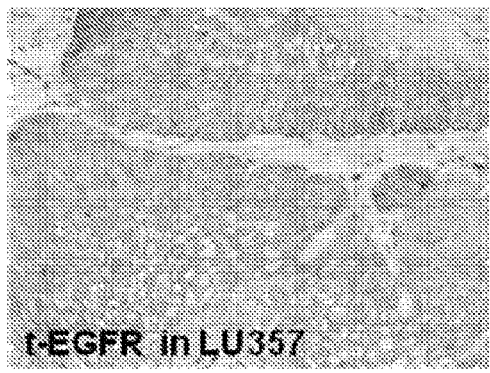
FIG. 4 shows EGFR-IHC staining of four representative NSCLC-HuPrime models (LU357, LU1204, LU1513, and LU387).
Figure 4:
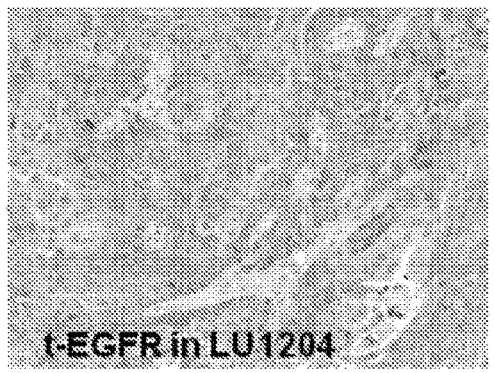
Figure 4:
Figure 4:
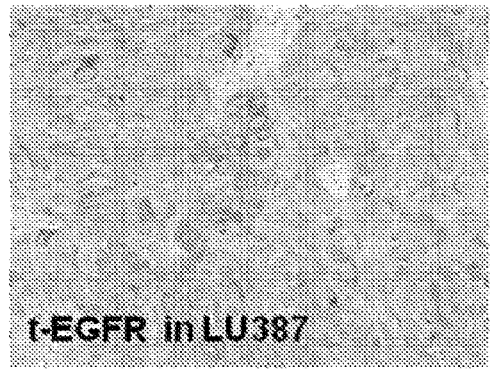

EGFR inhibitors. 2012; submitted). The results demonstrated that a subset of this cohort responded to cetuximab, similarly seen in the clinic (Khambata-Ford S, et al. *J Clin Oncol.* 2010; 28:918-27). 15/32 were found to be sensitive (as defined by % $^{\Delta T}/_{\Delta C}$<50%), or a response rate (RR) of 47% (Table 2). The examples of tumor growth inhibition curves of the responders and non-responders are shown in FIG. 2.

Next, the response rate (RR) of different histopathology subtypes was compared. Surprisingly, all responders were SCC (14/15) or PLC (1/15) (100%). The RR of SCC/PLC

TABLE 2

Summary of NSCLC HuPrime ® models

| Model | Pathology | EGFR mut | KRAS mut | EGFR expr (11725102_at) | MET CN (PennCNV) | Cetuximab ΔT/ΔC |
|---|---|---|---|---|---|---|
| 1235 | PLC | deletion | WT | +++ | 3 | −0.12 |
| 1868 | SCC | T790M/L858R | WT | ++ | 2 | −0.06 |
| 1204 | SCC | WT | WT | ++ | 2 | 0.03 |
| 357 | SCC | WT | WT | +++ | 2 | 0.04 |
| 387 | SCC | WT | WT | +++ | 2 | 0.08 |
| 330 | SCC | WT | WT | ++ | 2 | 0.11 |
| 1219 | SCC | WT | WT | ++ | 2 | 0.17 |
| 741 | SCC | WT | WT | +++ | 2 | 0.22 |
| 1160 | SCC | WT | WT | ++ | 2 | 0.22 |
| 395 | SCC | WT | WT | ++ | 2 | 0.23 |
| 9 | SCC | WT | WT |  | 1 | 0.35 |
| 1656 | SCC | WT | WT | +++ | 2 | 0.37 |
| 1143 | SCC | WT | WT | + | 2 | 0.37 |
| 1302 | SCC | WT | WT |  |  | 0.43 |
| 350 | SCC | WT | WT | +++ | 2 | 0.49 |
| 299 | SCC | WT | WT | + | 2 | 0.53 |
| 2505 | ADC | WT | WT | + | 2 | 0.57 |
| 2511 | LCC | WT | WT |  |  | 0.59 |
| 1901 | LCC | WT | WT | ++ | 4(amplified) | 0.77 |
| 1215 | Basal SCC | WT | WT |  | 2 | 0.80 |
| 1245 | ADC | WT | 35G > A, G12D | ++ | 2 | 0.82 |
| 1155 | SCC | WT | WT | + | 2 | 0.88 |
| 743 | SCC | WT | WT | ++ | 2 | 0.92 |
| 1225 | ADC | WT | WT |  |  | 0.94 |
| 2503 | ADC | WT | WT | ++ | 4(amplified) | 0.94 |
| 858 | ADC | L858R | WT | ++ | 4(amplified) | 0.97 |
| 377 | ADC | WT | WT | ++ | 1 | 1.00 |
| 387 | ADC | insertion | WT | +++ | 3 | 1.00 |
| 2512 | SCC | WT | Gly12Cys |  |  | 1.00 |
| 1429 | SCC |  |  |  |  | 1.00 |
| 697 | SCC | WT | WT | ++ | 2 | 1.04 |
| 1513 | SCC | WT | WT | + | 2 | 1.20 |

These 32 models samples were also confirmed to be EGFR positive per immunochemistry (IHC) analysis (Table 2 and FIG. 1), although it was not used as inclusion criterion for these studies. To assess the models for responses to cetuximab, this cohort was treated with a 1 mg/mouse dose level once weekly for two weeks. The tumor responses were measured by the tumor volume and quantified by % $^{\Delta T}/_{\Delta C}$ as previously described (Yang M, et al. Overcoming drug resistance with tailored treatment regimen in patient derived xenografts from naïve Asian NSCLC patients resistant to was 65% (15/23). Among the 17 non-responders, 7 were SCC (7/17, or 47%), 7 were ADC (7/17, or 41%), and 2 were LCC (12%). The RR for ADC was surprisingly low (0/7). This observation based on the limited number of samples suggested that SCC has significantly higher RR than that of ADC (p-value of 0.001 by 2-tailed independent t-test). NSCLC PDX models treated with cetuximab have been described previously by others (Fichtner I, et al. *Clin Cancer Res.* 2008; 14:6456-68 and Krumbach R, et al. *Eur J Cancer.* 2011; 47:1231-43). However, difference in responses among histology subtypes has never been reported or commented. This observation is unique to the model collection or a general phenomenon. It is worth noting that the models are treatment naïve, entirely Asian patient origins, with biased take-rate among histology subtypes, which may or may not contribute to potential differences in the observations.

The next question was whether there are clinical data that support this observation. There have been two clinical phase III studies where cetuximab combinations with chemotherapies were tested. In FLEX study, indeed somewhat better clinical benefit (OS) was observed for SCC as compared to that of AC with hazard ratios of 0.8 and 0.94, respectively, although not explicitly described in the report (Pirker R, et al. *Lancet.* 2009; 373:1525-31). In this study, the combination treatments were compared with chemotherapy alone.

Many factors can contribute to the potential discrepancy between trials on patients and PDX models, including 1) different types of endpoints—PFS (progress free survival) vs. RR, 2) different treatment regimens—combination vs single agent, 3) ethnic differences in population: largely Caucasian vs East Asian. Our observations provide significant medical implications.

The Activating EGFR Mutations in SCC have No Negative Effect on the Response to Cetuximab.

Next, the EGFR gene status of responders was examined in comparison to their responses to cetuximab. Among the top 4 responders (% $^{\Delta T}/_{AC}$<8%) (Table 2), three have classic activating EGFR mutations that were frequently reported in the clinic (Gazdar A F. *Oncogene.* 2009; 28 Suppl 1:S24-31). Specifically, they are HuPrime®-LU1868 containing L858RT790M double mutations, LU1235 containing deletion mutation (exon 19: 2236-2350), and LU1868/1235 were described in earlier reports (Yang M, et al. Overcoming drug resistance with tailored treatment regimen in patient derived xenografts from naïve Asian NSCLC patients resistant to EGFR inhibitors. 2012; submitted). These results further confirmed that the activating EGFR mutations have no negative influence on response to cetuximab, and that these mutations, along with the high expression of EGFR, were in fact positive factors contributing to the cetuximab response (Krumbach R, et al. *Eur J Cancer.* 2011; 47:1231-43 and Tsuchihashi Z, et al. *N Engl J Med.* 2005; 353:208-9).

Figure 5:
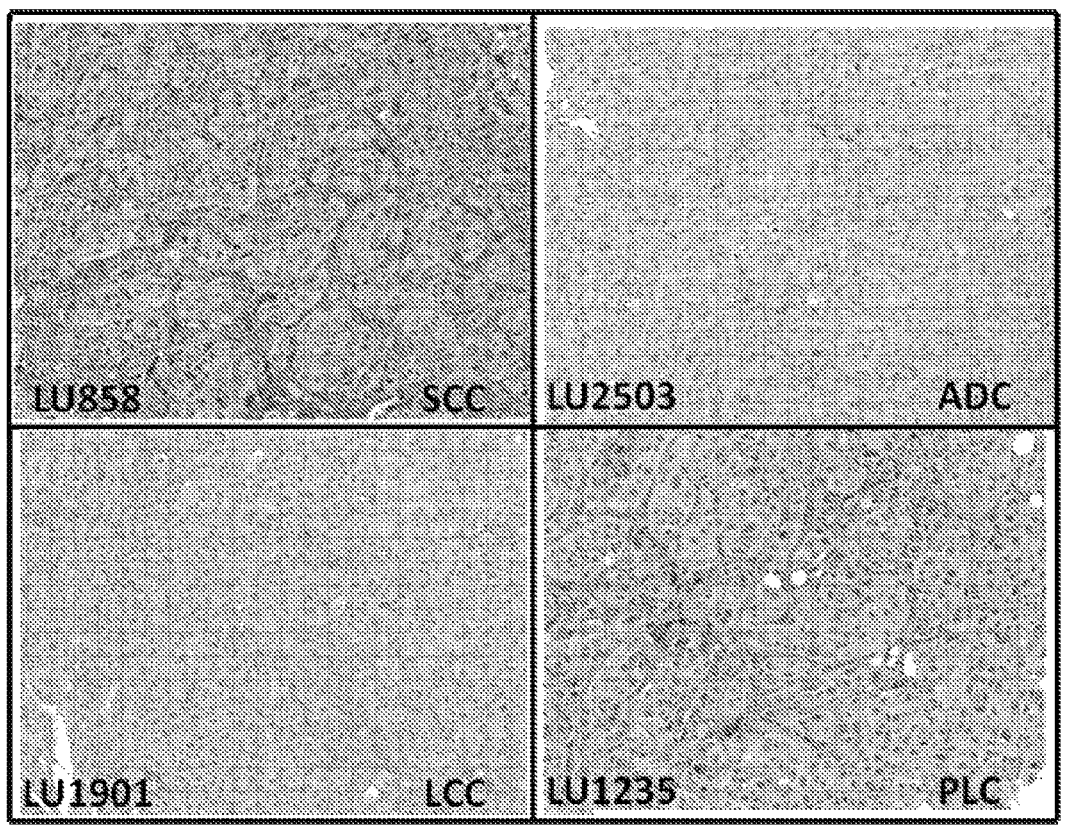
FIG. 5 shows histology subtypes of NSCLC—representative images.

Also interestingly, the models described above with EGFR mutations are SCC (Table 1 and Table 2), more than were found in ADC. This contradicts previous reports that EGFR mutations, while frequently found in ADC, are rarely found in SCC. This could represent a major difference between Asian and Caucasian NSCLC patients. In order to confirm this observation, several pathologists blindly and independently confirmed the histology of all these models. The H&E slides are shown in FIG. 5. In fact, there have been reports recently describing the EGFR point mutations in non-ADC (SCC, adenosquamous and large cell carcinoma), which occur in Chinese (Jia X L, et al. *Lung Cancer.* 2011; 74:396-400) and Japanese (Shukuya T, et al. *Cancer Sci.* 2011; 102:1032-7) patients.

Other oncogene mutations in the SCC responders have yet to be identified, except that LU1565 contains ALK-EML4 fusion and has % $^{\Delta T}/_{AC}$ value of 37%, or partial response. In contrast some other oncogenic mutations were found that are negative factors for cetuximab response in non-responsive SCC, including SCC-LU2512 (KRAS-G12C) (Table 2). In the non-SCC models, many of them were also found to have negative factors: ADC-LU858, ADC-LU2503 and LCC-LU1901 with c-Met amplification; ADC-LU1245 with KRAS-G12C; ADC-LU387 with amplification of Her2 gene.

The present study using PDX clearly demonstrated that high percentage of NSCLC SCC from Asian patients respond to cetuximab (Table 2).

Discussion

The only three approved target therapies are the TKIs against EGFR (erlotinib, gefitinib) and ALK-EML4 (crizotinib). They have limited applications since only a small percentage of NSCLC patients: 10% of NSCLCs for EGFR-TKIs (Lynch T J, et al. *N Engl J. Med.* 2004; 350:2129-39 and Paez J G, et al. *Science.* 2004; 304:1497-500), mainly in ADC subtype, and 3~5% for crizotinib (Rodig S J, et al. *Curr Opin Investig Drugs.* 2010; 11:1477-90). This renders extreme urgency of additional treatment options for NSCLC patients, particularly those marketed drugs but yet to be approved for this indication. Among them are monoclonal antibodies against EGFR, the same target of the two approved NSCLC drugs (EGFR-TKIs), including cetuximab and panitumumab (also not approved Matuzumab) being such potential options.

However, the clinical trials so far on cetuximab, largely conducted in the West, did not result in great promise. The major hurdle remains to identify predictive biomarkers and thus patient population that would be sensitive to cetuximab in clinical trial (Pirker R, et al. *Lancet.* 2009; 373:1525-31; Khambata-Ford S, et al. *J Clin Oncol.* 2010; 28:918-27; and O'Byrne K J, et al. *Lancet Oncol.* 2011; 12:795-805). Our present study using PDX clearly demonstrated that high percentage of NSCLC SCC from Asian patients respond to cetuximab (Table 1) and meets this hurdle. Our study can greatly help clinical study design, particularly the studies to be conducted in East Asia.

Particular attention has been paid to the finding that Asian NSCLC can be different from those of Caucasian. These have been seen as differences in: 1) the response to TKI (significant higher RR for Asian NSCLC (particularly female) than those in the West; 2) frequency of EGFR mutations in different histology subtypes as reported by others and here; 3) significant high RR in Asian SCC as described here. This new knowledge in the difference among the patient demographic helps to tailor more effective therapies.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

The invention claimed is:

1. A method for treating lung cancer in a patient based on histology of the lung cancer in the patient, wherein the lung cancer is Non-small cell lung cancer (NSCLC), consisting of administering to the patient an effective amount of a drug against epidermal growth factor receptor (EGFR), wherein the drug is cetuximab, and wherein the patient having NSCLC is identified to have squamous cell carcinoma (SCC) or pleiomorphic carcinoma (PLC), but not adenocarcinoma (ADC) or large cell carcinoma (LCC), and wherein the patient is of Asian descent.

2. A method for treating lung cancer in a patient based on histology of the lung cancer in the patient, wherein the lung cancer is Non-small cell lung cancer (NSCLC), consisting of determining the histology of the lung cancer, and administering to a patient identified to have squamous cell carcinoma (SCC) or pleiomorphic carcinoma (PLC), but not adenocarcinoma (ADC) or large cell carcinoma (LCC) a drug against epidermal growth factor receptor (EGFR), wherein the drug is cetuximab, and wherein the patient is of Asian descent.

* * * * *

SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: KRAS-Exon 2, F

<400> SEQUENCE: 1
ttatgtgtga catgttctaa t                                              21

<210> SEQ ID NO 2
<211> LENGTH: 21
<212> TYPE: DNA
<213> ORGANISM: Artificial Sequence
<220> FEATURE:
<223> OTHER INFORMATION: KRAS-Exon 2, R

<400> SEQUENCE: 2
agaatggtcc tgcaccagta a                                              21

<210> SEQ ID NO 3
<211> LENGTH: 20
<212> TYPE: DNA
<213> ORGANISM: Artificial Sequence
<220> FEATURE:
<223> OTHER INFORMATION: KRAS-Exon 3, F

<400> SEQUENCE: 3
tcaagtcctt tgcccatttt                                                20

<210> SEQ ID NO 4
<211> LENGTH: 20
<212> TYPE: DNA
<213> ORGANISM: Artificial Sequence
<220> FEATURE:
<223> OTHER INFORMATION: KRAS-Exon 3, R

<400> SEQUENCE: 4
tgcatggcat tagcaaagac                                                20

<210> SEQ ID NO 5
<211> LENGTH: 21
<212> TYPE: DNA
<213> ORGANISM: Artificial Sequence
<220> FEATURE:
<223> OTHER INFORMATION: KRAS-Exon 4, F

<400> SEQUENCE: 5
ttgtggacag gttttgaaag a                                              21

<210> SEQ ID NO 6
<211> LENGTH: 20
<212> TYPE: DNA
<213> ORGANISM: Artificial Sequence
<220> FEATURE:
<223> OTHER INFORMATION: KRAS-Exon 4, R

<400> SEQUENCE: 6
agaagcaatg ccctctcaag                                                20

<210> SEQ ID NO 7
<211> LENGTH: 20
<212> TYPE: DNA
<213> ORGANISM: Artificial Sequence

```
<220> FEATURE:
<223> OTHER INFORMATION: EGFR-Exon 18, F

<400> SEQUENCE: 7
catggtgagg gctgaggtga                                                    20

<210> SEQ ID NO 8
<211> LENGTH: 20
<212> TYPE: DNA
<213> ORGANISM: Artificial Sequence
<220> FEATURE:
<223> OTHER INFORMATION: EGFR-Exon 18, R

<400> SEQUENCE: 8
ccccaccaga ccatgagagg                                                    20

<210> SEQ ID NO 9
<211> LENGTH: 21
<212> TYPE: DNA
<213> ORGANISM: Artificial Sequence
<220> FEATURE:
<223> OTHER INFORMATION: EGFR-Exon 19, F

<400> SEQUENCE: 9
gtgcatcgct ggtaacatcc a                                                  21

<210> SEQ ID NO 10
<211> LENGTH: 23
<212> TYPE: DNA
<213> ORGANISM: Artificial Sequence
<220> FEATURE:
<223> OTHER INFORMATION: EGFR-Exon 19, R

<400> SEQUENCE: 10
ggagatgagc agggtctaga gca                                                23

<210> SEQ ID NO 11
<211> LENGTH: 20
<212> TYPE: DNA
<213> ORGANISM: Artificial Sequence
<220> FEATURE:
<223> OTHER INFORMATION: EGFR-Exon 20, F

<400> SEQUENCE: 11
cgcattcatg cgtcttcacc                                                    20

<210> SEQ ID NO 12
<211> LENGTH: 20
<212> TYPE: DNA
<213> ORGANISM: Artificial Sequence
<220> FEATURE:
<223> OTHER INFORMATION: EGFR-Exon 20, R

<400> SEQUENCE: 12
ctatcccagg agcgcagacc                                                    20

<210> SEQ ID NO 13
<211> LENGTH: 21
<212> TYPE: DNA
<213> ORGANISM: Artificial Sequence
<220> FEATURE:
<223> OTHER INFORMATION: EGFR-Exon 21, F

<400> SEQUENCE: 13
tggcatgaac atgaccctga a                                                  21
```

<210> SEQ ID NO 14
<211> LENGTH: 19
<212> TYPE: DNA
<213> ORGANISM: Artificial Sequence
<220> FEATURE:
<223> OTHER INFORMATION: EGFR-Exon 21, R

<400> SEQUENCE: 14
cagcctggtc cctggtgtc                                                19

<210> SEQ ID NO 15
<211> LENGTH: 19
<212> TYPE: DNA
<213> ORGANISM: Artificial Sequence
<220> FEATURE:
<223> OTHER INFORMATION: PI3K-Exon 1, F

<400> SEQUENCE: 15
ctccacgacc atcatcagg                                                19

<210> SEQ ID NO 16
<211> LENGTH: 26
<212> TYPE: DNA
<213> ORGANISM: Artificial Sequence
<220> FEATURE:
<223> OTHER INFORMATION: PI3K-Exon 1, R

<400> SEQUENCE: 16
gattacgaag gtattggttt agacag                                        26

<210> SEQ ID NO 17
<211> LENGTH: 22
<212> TYPE: DNA
<213> ORGANISM: Artificial Sequence
<220> FEATURE:
<223> OTHER INFORMATION: PI3K-Exon 9, F

<400> SEQUENCE: 17
gattggttct ttcctgtctc tg                                            22

<210> SEQ ID NO 18
<211> LENGTH: 26
<212> TYPE: DNA
<213> ORGANISM: Artificial Sequence
<220> FEATURE:
<223> OTHER INFORMATION: PI3K-Exon 9, R

<400> SEQUENCE: 18
ccacaaatat caatttacaa ccattg                                        26

<210> SEQ ID NO 19
<211> LENGTH: 21
<212> TYPE: DNA
<213> ORGANISM: Artificial Sequence
<220> FEATURE:
<223> OTHER INFORMATION: PI3K-Exon 20: F

<400> SEQUENCE: 19
tggggtaaag ggaatcaaaa g                                             21

<210> SEQ ID NO 20
<211> LENGTH: 20
<212> TYPE: DNA
<213> ORGANISM: Artificial Sequence
<220> FEATURE:
<223> OTHER INFORMATION: PI3K-Exon 20: R

<400> SEQUENCE: 20
cctatgcaat cggtctttgc                                                  20

<210> SEQ ID NO 21
<211> LENGTH: 18
<212> TYPE: DNA
<213> ORGANISM: Artificial Sequence
<220> FEATURE:
<223> OTHER INFORMATION: AKT-Exon 3, F

<400> SEQUENCE: 21
acatctgtcc tggcacac                                                    18

<210> SEQ ID NO 22
<211> LENGTH: 18
<212> TYPE: DNA
<213> ORGANISM: Artificial Sequence
<220> FEATURE:
<223> OTHER INFORMATION: AKT-Exon 3, R

<400> SEQUENCE: 22
gccagtgctt gttgcttg                                                    18

<210> SEQ ID NO 23
<211> LENGTH: 19
<212> TYPE: DNA
<213> ORGANISM: Artificial Sequence
<220> FEATURE:
<223> OTHER INFORMATION: BRAF-Exon 15, F

<400> SEQUENCE: 23
ctcttcataa tgcttgctc                                                   19

<210> SEQ ID NO 24
<211> LENGTH: 19
<212> TYPE: DNA
<213> ORGANISM: Artificial Sequence
<220> FEATURE:
<223> OTHER INFORMATION: BRAF-Exon 15, R

<400> SEQUENCE: 24
gtgaatactg ggaactatg                                                   19

<210> SEQ ID NO 25
<211> LENGTH: 20
<212> TYPE: DNA
<213> ORGANISM: Artificial Sequence
<220> FEATURE:
<223> OTHER INFORMATION: ERK-Exon 2, F

<400> SEQUENCE: 25
actttaccaa cttgccttct                                                  20

<210> SEQ ID NO 26
<211> LENGTH: 18
<212> TYPE: DNA
<213> ORGANISM: Artificial Sequence
<220> FEATURE:
<223> OTHER INFORMATION: ERK-Exon 2, R

<400> SEQUENCE: 26
tcacaacaaa ccatccct                                                    18

<210> SEQ ID NO 27

```
<211> LENGTH: 15
<212> TYPE: DNA
<213> ORGANISM: Artificial Sequence
<220> FEATURE:
<223> OTHER INFORMATION: ERK-Exon 8, F

<400> SEQUENCE: 27
tgccttaccc ataac                                                        15

<210> SEQ ID NO 28
<211> LENGTH: 19
<212> TYPE: DNA
<213> ORGANISM: Artificial Sequence
<220> FEATURE:
<223> OTHER INFORMATION: ERK-Exon 8, R

<400> SEQUENCE: 28
ggaccttgag gaacataat                                                    19
```